US009488621B2

(12) United States Patent
Kaduchak et al.

(10) Patent No.: US 9,488,621 B2
(45) Date of Patent: *Nov. 8, 2016

(54) PARTICLE ANALYSIS IN AN ACOUSTIC CYTOMETER

(75) Inventors: Gregory Kaduchak, Los Alamos, NM (US); Michael D Ward, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 492 days.

This patent is subject to a terminal disclaimer.

(21) Appl. No.: 13/571,662

(22) Filed: Aug. 10, 2012

(65) Prior Publication Data

US 2012/0298564 A1 Nov. 29, 2012

Related U.S. Application Data

(63) Continuation of application No. 12/283,491, filed on Sep. 11, 2008, now Pat. No. 8,266,951.

(60) Provisional application No. 61/008,422, filed on Dec. 19, 2007.

(51) Int. Cl.
*G01N 1/20* (2006.01)
*G01N 15/10* (2006.01)
*G01N 37/00* (2006.01)
*G01N 29/14* (2006.01)
(Continued)

(52) U.S. Cl.
CPC ......... *G01N 29/14* (2013.01); *B01L 3/502761* (2013.01); *G01N 15/1404* (2013.01); *G01N 33/4833* (2013.01); *B01L 2200/0636* (2013.01); *B01L 2200/0652* (2013.01); *B01L 2300/0838* (2013.01); *B01L 2300/0864* (2013.01); *B01L 2400/0439* (2013.01); *B01L 2400/0487* (2013.01); *G01N 15/1459* (2013.01); *G01N 15/1463* (2013.01); *G01N 2001/4094* (2013.01); *G01N 2015/1081* (2013.01); *G01N 2015/142* (2013.01); *G01N 2015/149* (2013.01); *G01N 2015/1415* (2013.01)

(58) Field of Classification Search
CPC .............. G01N 15/1404; G01N 15/1459; G01N 2015/149; G01N 15/1463; G01N 2015/142
USPC .................. 73/570.5, 61.75, 64.56
See application file for complete search history.

(56) References Cited

U.S. PATENT DOCUMENTS 2,900,536 A 8/1959 Palo
3,882,732 A 5/1975 Fletcher et al.
(Continued)

FOREIGN PATENT DOCUMENTS

CN 1493831 A 5/2004
CN 1524948 9/2004
(Continued)

OTHER PUBLICATIONS

U.S. Appl. No. 11/982,042: Non-Final Office Action dated Oct. 22, 2013.
(Continued)

*Primary Examiner* — Laura Martin
*Assistant Examiner* — Rose M Miller
(74) *Attorney, Agent, or Firm* — Baker & Hostetler LLP

(57) ABSTRACT

The present invention is a method and apparatus for acoustically manipulating one or more particles.

4 Claims, 6 Drawing Sheets

(51) Int. Cl.
  *G01N 15/14*  (2006.01)
  *G01N 33/483*  (2006.01)
  *B01L 3/00*  (2006.01)
  *G01N 1/10*  (2006.01)
  *B01D 15/08*  (2006.01)
  *G01N 1/40*  (2006.01)

(56) References Cited

U.S. PATENT DOCUMENTS

| | | |
|---|---|---|
| 4,055,491 A | 10/1977 | Porath-Furedi |
| 4,265,124 A | 5/1981 | Lim et al. |
| 4,285,810 A | 8/1981 | Kirkland et al. |
| 4,350,683 A | 9/1982 | Galfre et al. |
| 4,434,230 A | 2/1984 | Ritts, Jr. |
| 4,492,752 A | 1/1985 | Hoffman et al. |
| 4,523,682 A | 6/1985 | Barmatz et al. |
| 4,523,982 A | 6/1985 | Lee |
| 4,596,464 A | 6/1986 | Hoffman et al. |
| 4,604,542 A | 8/1986 | Thompson |
| 4,673,512 A | 6/1987 | Schram |
| 4,743,361 A | 5/1988 | Schram |
| 4,759,775 A | 7/1988 | Peterson et al. |
| 4,777,823 A | 10/1988 | Barmatz et al. |
| 4,790,653 A | 12/1988 | North, Jr. |
| 4,845,025 A | 7/1989 | Lary et al. |
| 4,867,559 A | 9/1989 | Bach |
| 4,877,516 A | 10/1989 | Schram |
| 4,913,883 A | 4/1990 | Imai et al. |
| 4,964,303 A | 10/1990 | Barmatz et al. |
| 4,979,824 A | 12/1990 | Mathies et al. |
| 4,987,086 A | 1/1991 | Brosnan et al. |
| 4,991,923 A | 2/1991 | Kino et al. |
| 5,006,266 A | 4/1991 | Schram |
| 5,030,002 A | 7/1991 | North, Jr. |
| 5,032,381 A | 7/1991 | Bronstein et al. |
| 5,040,890 A | 8/1991 | North, Jr. |
| 5,079,959 A | 1/1992 | Miyake et al. |
| 5,085,783 A | 2/1992 | Feke et al. |
| 5,106,187 A | 4/1992 | Bezanson |
| 5,164,094 A | 11/1992 | Stuckart |
| 5,225,089 A | 7/1993 | Benes et al. |
| 5,264,906 A | 11/1993 | Ferer et al. |
| 5,346,670 A | 9/1994 | Renzoni et al. |
| 5,376,551 A | 12/1994 | Yoshikami |
| 5,395,588 A | 3/1995 | North, Jr. et al. |
| 5,430,541 A | 7/1995 | Sapp |
| 5,491,344 A | 2/1996 | Kenny et al. |
| 5,504,337 A | 4/1996 | Lakowicz et al. |
| 5,527,460 A | 6/1996 | Trampler et al. |
| 5,528,045 A | 6/1996 | Hoffman et al. |
| 5,547,849 A | 8/1996 | Baer et al. |
| 5,626,767 A | 5/1997 | Trampler et al. |
| 5,644,388 A | 7/1997 | Maekawa et al. |
| 5,674,698 A | 10/1997 | Zarling et al. |
| 5,688,406 A | 11/1997 | Dickinson et al. |
| 5,690,895 A | 11/1997 | Matsumoto et al. |
| 5,711,888 A | 1/1998 | Trampler et al. |
| 5,739,902 A | 4/1998 | Gjelsnes et al. |
| 5,798,222 A | 8/1998 | Goix |
| 5,800,861 A | 9/1998 | Chiang et al. |
| 5,831,166 A | 11/1998 | Kozuka et al. |
| 5,902,489 A | 5/1999 | Yasuda et al. |
| 5,915,925 A | 6/1999 | North |
| 5,981,180 A | 11/1999 | Chandler et al. |
| 6,003,388 A | 12/1999 | Oeftering |
| 6,055,859 A | 5/2000 | Kozuka et al. |
| 6,074,879 A | 6/2000 | Zelmanovic et al. |
| 6,090,295 A | 7/2000 | Raghavarae et al. |
| 6,197,593 B1 | 3/2001 | Deka et al. |
| 6,216,538 B1 | 4/2001 | Yasuda et al. |
| 6,221,258 B1 | 4/2001 | Feke et al. |
| 6,228,652 B1 | 5/2001 | Rodriguez et al. |
| 6,245,207 B1 | 6/2001 | Yasuda et al. |
| 6,248,590 B1 | 6/2001 | Malachowski |
| 6,255,118 B1 | 7/2001 | Alfano et al. |
| 6,309,886 B1 | 10/2001 | Ambrose et al. |
| 6,332,541 B1 | 12/2001 | Coakley et al. |
| 6,348,687 B1 | 2/2002 | Brockmann et al. |
| 6,373,567 B1 | 4/2002 | Wise et al. |
| 6,449,563 B1 | 9/2002 | Dukhin et al. |
| 6,467,350 B1 | 10/2002 | Kaduchak et al. |
| 6,532,061 B2 | 3/2003 | Ortyn et al. |
| 6,549,275 B1 | 4/2003 | Cabuz et al. |
| 6,565,727 B1 | 5/2003 | Shenderov et al. |
| 6,592,821 B1 | 7/2003 | Wada et al. |
| 6,604,435 B2 | 8/2003 | Buchanan et al. |
| 6,644,118 B2 | 11/2003 | Kaduchak et al. |
| 6,647,739 B1 | 11/2003 | Kim |
| 6,668,664 B1 | 12/2003 | Ohkawa |
| 6,683,314 B2 | 1/2004 | Oostman, Jr. et al. |
| 6,713,019 B2 | 3/2004 | Ozasa et al. |
| 6,736,904 B2 | 5/2004 | Poniatowski et al. |
| 6,773,556 B1 | 8/2004 | Brockie et al. |
| 6,794,671 B2 | 9/2004 | Nicoli et al. |
| 6,797,158 B2 | 9/2004 | Feke et al. |
| 6,813,017 B1 | 11/2004 | Hoffman et al. |
| 6,816,257 B2 | 11/2004 | Goix |
| 6,831,279 B2 | 12/2004 | Ho |
| 6,881,314 B1 | 4/2005 | Wang et al. |
| 6,911,082 B2 | 6/2005 | Sato et al. |
| 6,929,750 B2 | 8/2005 | Laurell et al. |
| 6,949,355 B2 | 9/2005 | Yamanishi et al. |
| 6,982,165 B2 | 1/2006 | Yamakawa et al. |
| 7,008,540 B1 | 3/2006 | Weavers et al. |
| 7,018,819 B2 | 3/2006 | Orwar et al. |
| 7,047,809 B2 | 5/2006 | Cobb |
| 7,052,864 B2 | 5/2006 | Durkop et al. |
| 7,064,823 B2 | 6/2006 | Roche et al. |
| 7,081,192 B2 | 7/2006 | Wang et al. |
| 7,091,348 B2 | 8/2006 | O'Neill et al. |
| 7,108,137 B2 | 9/2006 | Lal et al. |
| 7,113,266 B1 | 9/2006 | Wells |
| 7,161,665 B2 | 1/2007 | Johnson |
| 7,166,443 B2 | 1/2007 | Walker et al. |
| 7,190,832 B2 | 3/2007 | Frost et al. |
| 7,255,780 B2 | 8/2007 | Shenderov |
| 7,262,838 B2 | 8/2007 | Fritz |
| 7,267,798 B2 | 9/2007 | Chandler |
| 7,315,357 B2 | 1/2008 | Ortyn et al. |
| 7,329,545 B2 | 2/2008 | Pamula et al. |
| 7,340,957 B2 | 3/2008 | Kaduchak et al. |
| 7,362,432 B2 | 4/2008 | Roth |
| 7,373,805 B2 | 5/2008 | Hawkes et al. |
| 7,403,125 B2 | 7/2008 | Rich |
| 7,431,892 B2 | 10/2008 | Zumeris et al. |
| 7,452,725 B2 * | 11/2008 | Leary et al. ............ 436/63 |
| 7,477,363 B2 | 1/2009 | Nagai |
| 7,479,630 B2 | 1/2009 | Bandura et al. |
| 7,570,676 B2 | 8/2009 | Essaian et al. |
| 7,758,811 B2 | 7/2010 | Durack et al. |
| 7,835,000 B2 | 11/2010 | Graves et al. |
| 7,837,040 B2 | 11/2010 | Ward et al. |
| 7,990,525 B2 | 8/2011 | Kanda |
| 8,075,786 B2 | 12/2011 | Bagajewicz |
| 8,083,068 B2 | 12/2011 | Kaduchak et al. |
| 8,134,705 B2 | 3/2012 | Kaduchak et al. |
| 8,227,257 B2 | 7/2012 | Ward et al. |
| 8,263,407 B2 | 9/2012 | Goddard et al. |
| 8,266,950 B2 | 9/2012 | Kaduchak et al. |
| 8,266,951 B2 | 9/2012 | Kaduchak et al. |
| 8,309,408 B2 | 11/2012 | Ward et al. |
| 2003/0059850 A1 | 3/2003 | Evans |
| 2004/0065599 A1 | 4/2004 | Lal et al. |
| 2004/0069717 A1 | 4/2004 | Laurell et al. |
| 2005/0072677 A1 | 4/2005 | Gascoyne et al. |
| 2005/0097968 A1 | 5/2005 | Ishikawa et al. |
| 2006/0006769 A1 | 1/2006 | Masters et al. |
| 2006/0034733 A1 | 2/2006 | Ferren et al. |
| 2006/0071580 A1 | 4/2006 | Sawada |
| 2006/0163166 A1 | 7/2006 | Hawkes et al. |
| 2007/0037172 A1 | 2/2007 | Chiu et al. |
| 2007/0071683 A1 | 3/2007 | Dayton et al. |

(56) References Cited

U.S. PATENT DOCUMENTS

| | | | |
|---|---|---|---|
| 2007/0098232 | A1 | 5/2007 | Matula et al. |
| 2007/0119239 | A1* | 5/2007 | Priev et al. .................. 73/61.75 |
| 2009/0029870 | A1 | 1/2009 | Ward et al. |
| 2009/0038932 | A1 | 2/2009 | Denslow et al. |
| 2009/0042239 | A1 | 2/2009 | Ward et al. |
| 2009/0045107 | A1 | 2/2009 | Ward et al. |
| 2009/0053686 | A1 | 2/2009 | Ward et al. |
| 2009/0107241 | A1 | 4/2009 | Goddard et al. |
| 2009/0178716 | A1 | 7/2009 | Kaduchak et al. |
| 2009/0227042 | A1 | 9/2009 | Gauer et al. |
| 2009/0316151 | A1 | 12/2009 | Matula et al. |
| 2010/0000325 | A1 | 1/2010 | Kaduchak et al. |
| 2010/0009333 | A1 | 1/2010 | Auer |
| 2011/0024335 | A1 | 2/2011 | Ward et al. |
| 2011/0032522 | A1 | 2/2011 | Graves et al. |
| 2011/0134426 | A1 | 6/2011 | Kaduchak et al. |

FOREIGN PATENT DOCUMENTS

| | | |
|---|---|---|
| CN | 1221309 | 10/2005 |
| CN | 1739020 A | 2/2006 |
| CN | 1795382 | 6/2006 |
| CN | 101060898 | 10/2007 |
| DE | 3027433 | 2/1982 |
| EP | 0 147 032 | 3/1985 |
| EP | 0 292 470 | 11/1988 |
| EP | 0 773 055 | 5/1997 |
| EP | 1 416 239 | 5/2004 |
| FR | 821419 | 12/1937 |
| GB | 500271 | 12/1937 |
| JP | 363139231 A | 6/1988 |
| JP | 01-112161 | 4/1989 |
| JP | 406241977 A | 9/1994 |
| JP | 07-047259 | 2/1995 |
| JP | 07-318476 | 12/1995 |
| JP | 08-266891 | 10/1996 |
| JP | 408266891 A | 10/1996 |
| JP | 09-288052 | 11/1997 |
| JP | 10-082723 | 3/1998 |
| JP | 11-014533 | 1/1999 |
| JP | 11-197406 | 7/1999 |
| JP | 11-326155 | 11/1999 |
| JP | 11-352048 | 12/1999 |
| JP | 2002-22531 | 1/2002 |
| JP | 2007-285908 | 11/2007 |
| JP | 2007-530924 | 2/2011 |
| RU | 2224992 | 2/2004 |
| WO | WO 88/09210 | 12/1988 |
| WO | WO 90/05008 | 5/1990 |
| WO | WO 94/29695 | 12/1994 |
| WO | WO 97/02482 | 1/1997 |
| WO | WO 99/42810 | 8/1999 |
| WO | WO 00/04978 | 2/2000 |
| WO | WO 00/41794 | 7/2000 |
| WO | WO 02/059577 | 8/2002 |
| WO | WO 02/072234 | 9/2002 |
| WO | WO 02/072236 | 9/2002 |
| WO | WO 03/079006 | 9/2003 |
| WO | WO 2004/024287 | 3/2004 |
| WO | WO 2004/033087 | 4/2004 |
| WO | WO 2004/048948 | 6/2004 |
| WO | WO 2004/088283 | 10/2004 |
| WO | WO 2005/093784 | 10/2005 |
| WO | WO 2006/031299 | 3/2006 |
| WO | WO 2006/032048 A2 | 3/2006 |
| WO | WO 2006/032703 | 3/2006 |
| WO | WO 2006/076195 | 7/2006 |
| WO | WO 2007/083295 A2 | 7/2007 |
| WO | WO 2007/128795 | 11/2007 |
| WO | WO 2007/128795 A2 | 11/2007 |
| WO | WO 2008/122051 | 10/2008 |
| WO | WO 2009/086043 | 7/2009 |
| WO | WO 2009/091925 | 7/2009 |
| WO | WO 2011/068764 | 6/2011 |

OTHER PUBLICATIONS

U.S. Appl. No. 13/966,624: Non-Final Office Action dated Sep. 24, 2013.
U.S. Appl. No. 13/571,629: Restriction Requirement dated Dec. 6, 2013, 10 pages.
U.S. Appl. No. 13/618,237: Non-Final Office Action dated Jan. 27, 2014, 13 pages.
U.S. Appl. No. 13/966,624: Final Office Action dated Jan. 28, 2014, 15 pages.
U.S. Appl. No. 12/903,042: Final Office Action dated May 24, 2013.
U.S. Appl. No. 13/295,934: Non-Final Office Action dated May 24, 2013.
Aboobaker, N. et al., "Mathematical modeling of the movement of suspended particles subjected to acoustic and flow fields", *App. Math. Modeling*, 2005, 29, 515-532.
Aleksandrov, et al., "Pulsed Laser Florescence Spectrometer," Zhurnal Prikladnoi Spektroskopii, Oct. 1987, 47(4), 686-692.
Anderson, M. et al., "The Physics and Technology of Ultrasonic Particle Separation in Air", *WCU*, 2003, 1615-1621.
Apfel, R.E. et al., "Acoustic Radiation Pressure—Principles and Application to Separation Science", *Fortschritte Der Akustik DAGA '90*, 1990, 19-30.
Araz, M.K. et al., "Ultrasonic Separation in Microfluidic Capillaries", *IEEE Ultrasonics Symposium*, 2003, 1066-1069.
Asai, M.K. et al., "Ultrasonic Treatment of Slurry," Third International Coal Preparation Conference, 1958, 518-527.
Bardsley, et al., "Electroacoustic Productions of Murine Hybridomas," Journal of Immunological Methods, 129(1), 1990, 41-47.
Barmatz, M. et al., "Acoustic radiation potential on a sphere in plane, cylindrical, and spherical standing wave fields", *J. Acoust. Soc. Am.*, 1985, 77, 928-945.
Bauerecker, S. et al., "Formation and growth of ice particles in stationary ultrasonic fields", *J. of Chem. Phys.*, 1998, 3709-3712.
Bazou, D. et al., "Physical Environment of 2-D Animal Cell Aggregates Formed in a Short Pathlength Ultrasound Standing Wave Trap", *Ultrasound in Med. & Biol.*, 2005, 31, 423-430.
Benes, "Separation of Dispersed Particles by Ultrasonic-Induced Coagulation", 15th Conference of the German Society for Acoustics, 1989, 2 pages.
Benes, E. et al., "Improved quartz crystal microbalance technique", *J. Appl. Phys.*, 1984, 56, 608-626.
Beverloo, H.B. et al., "Inorganic Phsophors as New Luminescent Labels for Irnmunocytochernistry and Time-Resolved Microscopy", *Cytometry*, 1990, 11, 784-792.
Bienvenue, J.M. et al., "Microchip-Based Cell Lysis and DNA Extraction from Sperm Cells for Application to Forensic Analysis", *J. Forensic Sci.*, 2006, 51, 266-273.
Binks, B.P. et al., "Modern Aspects of Emulsion Science", *The Royal Society of Chemistry*, 1998, 310-321.
Bishop, J.E. et al., "Mechanism of higher brightness of PerCP-Cy5. 5", *Cytometry Supp*, 2000, 10, 162-163.
Borgnis, "Acoustic Radiation Pressure of Plane Compressional Waves," *Reviews of Modern Physics*, Jul. 1953, 25(3),653-664.
Borisov, S.M. et al., "Blue LED Excitable Temperature Sensors Based ona New Eurpium (III) Chelate," *J. Fluoresc.*, 2008, 18, 581-589.
Borthwick, K.A. et al., "Development of a novel compact sonicator for cell disruption", *J. of Microbioloaical Methods*, 2005, 60, 207-216.
Bosma, R. et al., "Ultrasound, a new separation technique to harvest microlalgae", *J. Appl. Phycology*, 2003, 15, 143-153.
Bossuyt, X. et al., "Comparative Analysis for Whole Blood Lysis Methods for Flow Cytometry", *Cytometry*, 1997, 30, 124-133.
Brodeur, P. H., "Acoustic Separation in a Laminar Flow," Ultrasonics Symposium, 1994, 1359-1362.
Caperan, P.H. et al., "Acoustic Agglomeration of a Glycol Fog Aerosol: Influence of Particle Concentration and Intensity of the Sound Field at Two Frequencies", *J. Aerosol Sci.*, 1995, 26, 595-612.

(56) References Cited

OTHER PUBLICATIONS

Chase, E.S. et al., "Resolution of Dimly Fluorescent Particles: A Practical Measure of Fluorescence Sensitivity", *Cytometry*, 1998, 33, 267-279.

Cheung, et al., "Impedance Spectroscopy Flow Cytometry: On-Chip Label-Free Cell Differentiation," *Cytometry Part A*, Feb. 10, 2005, 65A, 124-132.

Coakley, W.T. et al., "Cell-cell contact and membrane spreading in an ultrasound trap", *Colloids and Surfaces B: Biointerfaces*, 2004, 34, 221-230.

Coakley, W.T. et al., "Ultrasonic separations in analytical biotechnology", *Tibtech*, 1997, 15, 506-511.

Coakley, W.T. et al., "Analytical scale ultrasonic standing wave manipulation of cells and microparticles", *Ultrasonics*, 2000, 38, 638-641.

Condrau, M.A. et al., "Time-Resolved Flow Cytometry for the Measurement of Lanthanide Chelate Fluorescence: I. Concept and Theoretical Evaluation", *Cytometry*, 1994, 16, 187-194.

Condrau, M.A. et al., "Time-Resolved Flow Cytometry for the Measurement of Lanthanide Chelate Fluorescence: II. Instrument Design and Experimental Results", *Cytometry*, 1994, 16, 195-205.

Cousins, C.M. et al., "Plasma Preparation from Whole Blood Using Ultrasound", *Ultrasound in Med. & Biol.*, 2000, 26, 881-888.

Curtis, H.W. et al., "Ultrasonic Continuous Flow Plasmapheresis Separator", *IBM Tech. Disc. Bulletin*, 1982, 25,192-193.

Czyz, H. et al., "On the Concentration of Aerosol Particles by Means of Drift Forces in a Standing Wave Field", *Acustica*, 1990, 70, 23-28.

Dain, Y. et al., "Dynamics of Suspended Particles in a Two-Dimensional High-Frequency Sonic Field", *J. Aerosol Sci.*, 1995, 26, 575-594.

Dain, Y. et al., "Side drift of aerosols in two-dimensional resonant acoustic levitators", *J. Acoust. Soc. Am*, 1997, 102, 2549-2555.

Danilov, S D. et al., "Mean force on a small sphere in a sound field in a viscous fluid", *J. Acoust. Soc. Am.*, 2000, 107, 143-1 53.

Danilov, S.D. et al., "The Mean Force Acting on a Small Body in an Axisymmetric Sound Field in a Real Medium", *Izvestiva Adademii Nauk SSSR, Mekhanika Zhidkosti I Gaza*, 1985, 5, 812-820.

Dean, P.N. et al., "Hydrodynamic Orientation of Sperm Heads for Flow Cytometry", *Biophys. J.*, 1978, 23, 7-13.

Doblhoff-Dier, 0. et al., "A Novel Ultrasonic Resonance Field Device for the Retention of Animal Cells", *Biotechnol. Prog.*, 1994, 10, 428-432.

Doinikov, A.A. et al., "Acoustic radiation force on a spherical particle in a viscous heat-conducting fluid. I. General formula", *J. Acoust. Soc. Am.*, 1997, 101, 713-721.

Doinikov, A.A. et al., "Acoustic radiation force on a spherical particle in a viscous heat-conducting fluid. II. Force on a rigid sphere", *J. Acoust. Soc. Am.*, 1997, 101, 722-730.

Doinikov, A.A. et al., "Acoustic radiation force on a spherical particle in a viscous heat-conducting fluid. III. Force on a liquid drop", *J. Acoust. Soc. Am.*, 1997, 101, 731-740.

Doinikov, A.A. et al., "Acoustic radiation pressure on a rigid sphere in a viscous fluid", *Proc. R. Soc. Lond.*, 1994, 447-466.

Donnert, G. et al., "Major signal increase in fluorescence microscopy through dark-state relaxation", *Nature Methods*, 2007, 4, 81-86.

Doornbos, R.M. et al., "Experimental and Model Investigations of Bleaching and Saturation of Fluorescence in Flow Cytometry", *Cytometry*, 1997, 29,204-214.

Fenniri, H. et al., "Classification of Spectroscopically Encoded Resins by Raman Mapping and Infrared Hyperspectral Imaging", *Journal of Combinatorial Chemistry*, 2006, 8, 192-198.

Fulwyler, M.J. et al., "Hydronamic Orientation of Cells", *Histochem.Cytoche.*, 1977, 7, 781-783.

Gaida, T.H. et al., "Selective Retention of Viable Cells in Ultrasonic Resonance Field Devices", *Biotech. Prog.*, 1996, 12, 73-76.

Gao, X. et al., "Quantum Dot-Encoded Mesoporous Beads with High Brightness and Uniformity: Rapid Readout Using Flow Cytometry", *Anal. Chem.*, 2004, 3, 2406-2410.

Gherardini, L. et al., "A New Immobilisation Method to Arrange Particles in a Gel Matrix by Ultrasound Standing Waves", *Ultrasound in Med. & Biol.*, 2005, 31, 261-272.

Goddard, G.R. et al., "Ultrasonic Concentration in a Line Driven Cylindrical Tube", *Dissertation*, 2004, 1-276.

Goddard, G. et al., "Single Particle High Resolution Spectral Analysis Flow Cytometry", *Cytometry*, 2006, 69A, 842-851.

Goddard, G. et al., "Ultrasonic particle concentration in a line-driven cylindrical tube", *J. Acoust. Soc. Am.*, 2005, 117, 3440-3447.

Goddard, G. et al., "Ultrasonic Particle-Concentration for Sheathless Focusing of Particles for Analysis in a Flow Cytometer", *Cytometry*, 2006, 69, 66-74.

Gonzalez, I. et al., "Precise Measurements of Particle Entertainment in a Standing-Wave Acoustic Field Between 20 and 3500 Hz", *J. Aerosol Sci.*, 2000, 31,1461-1468.

Gor'Kov, L.P. et al., "On the forces acting on a small particle in an acoustical field in an ideal fluid", *Soviet Physics-Doklady*, 1962, 6, 773-775.

Gould, R.K. et al., "Upper sound pressure limits on particle concentration in fields of ultrasonic standing-wave at megahertz frequencies", *Ultrasonics*, 1992, 30, 239-244.

Gould, R.K. et al., "The effects of acoustic forces on small particles in suspension", *Proceedings of the 1973 Symposium on Finite Amplitude Wave Effects in Fluids*, Bjorno, L., ed., Pergamon, Guildford, 1974, 252-257.

Groschl, "Automatic frequency control for piezoelectric resonators and their implementation in the acoustic driftwave resonator", Thesis implemented at the Institute for General Physics the Technical University of Vienna, Nov. 1991, 2 pages.

Grossner, M.T. et al., "Single fiber model of particle retention in an acoustically driven porous mesh", *Ultrasonics*, 2003, 41, 65-74.

Grossner, M.T. et al., "Single-Collector Experiments and Modeling of Acoustically Aided Mesh Filtration", *Amer. Inst. of Chem. Eng.*, 2005, 51, 1590-1598.

Grossner, M.T. et al., "Transport analysis and model for the performace of an ultrasonically enhanced filtration process", *Chem. Ena. Sci.*, 2005, 60, 3233-3238.

Gupta, S. et al., "Acoustically driven collection of suspended particles within porous media", *Ultrasonics*, 1997, 35, 131-139.

Gupta, S. et al., "Fractionation of Mixed Particulate Solids According to Compressibility Using Ultrasonic Standing Wave Fields", *Chem. Eng. Sci.*, 1995, 50, 3275-3284.

Haake, A. et al., "Contactless micromanipulation of small particles by an ultrasound field excited by a vibrating body", *J. Acoust. Soc. Am.*, 2005, 117, 2752-2760.

Haake, A. et al., "Manipulation of Cells Using an Ultrasonic Pressure Field", *Ultrasound in Med. & Biol.*, 2005, 31, 857-864.

Haake, A. et al., "Positioning of small particles by an ultrasound field excited by surface waves", *Ultrasonics*, 2004, 42, 75-80.

Haake, et al., "Positioning, Displacement, and Localization of Cells Using Ultrasonic Forces," Biotechnology and Bioengineering, 92(1), Aug. 10, 2005, 8-14.

Habbersett, R.C. et al., "An Analytical System Based on a Compact Flow Cytometer for DNA Fragment Sizing and Single Molecule Detection", *Cytometry* 2004, 60A,125-134.

Hager, F. et al., "A Summary of All Forces Acting on Spherical Particles in a Sound Field", *Proc. of the Ultrasonic International '91 Conference and Exhibition*, Le Touauet, France, 1991, 1-4.

Hamilton, M.F. et al., "Acoustic streaming generated by standing waves in two-dimensional channels of arbitrary width", *J. Acoust. Soc. Am.*, 2003, 113, 153-160.

Hamilton, M.F. et al., "Linear and nonlinear frequency shifts in acoustical resonators with varying cross sections", *J. Acoust. Soc. Am.*, 2001, 110, 109-119.

Hancock, A., "Observation of Forces on Microparticles in Acoustic Standing Waves", *Thesis, submitted in partial satisfaction of the reaquirements for the degree of Master of Science in Biomedical Engineering*, University of California, Davis, 2001, 1-155.

(56) References Cited

OTHER PUBLICATIONS

Harma, H. et al., "Zeptomole detection sensitivity of prostate-specific antigen in a rapid microtitre plate assay using time-resolved fluorescence", *Luminescence*, 2000, 15, 351-355.
Harris, N.R. et al., "A silicon microfluidic ultrasonic separator", *Sensors and Actuators*, 2004, 95, 425-434.
Harrison, B.S. et al., "Near-Infrared Photo- and Electroluminescence of Alkoxy-Substituted Poly (p-phenylene) and Nonconjugated Polymer/Lanthanide Tetraphenylporphyrin Blends", *Chemistry of Materials*, 2004, 16, 2938-2947.
Hatanaka, S-I et al., "Effect of Process Parameters on Ultrasonic Separation of Dispersed Particles in Liquid", *Jpn. J. ADPI. Phvs.*, 1999, 38, 3096-3100.
Hawkes, et al., "Continuous Cell Washing and Mixing Driven by an Unltrsound Standing Wave Within a Microfluidic Channel," Lab Chip, 4, Sep. 27, 2004, 446-452.
Hawkes, J.J. et al., "Force field particle filter, combinin ultrasound standing waves and laminar flow", *Sensors and Actuators B*, 2001, 75, 213-222.
Hawkes, J.J. et al., "Microparticle manipulation in millimetre scale ultrasonic standind wave chambers", *Ultrasonics*, 1998, 36, 925-931.
Hawkes, J.J. et al., "Single half-wavelength ultrasonic particle filter: Predictions of the transfer matrix multilayer resonator model and experimental filtration results", *J. Acoust. Soc. Am.*, 2002, 111, 1259-1266.
Hawkes, J.J. et al., "A laminar flow expansion chamber facilitating downstream manipulation of particles concentrated using an ultrasonic standing wave", *Ultrasonics*, 1998, 36, 901-903.
Hawkes, J.J. et al., "Ultrasonic deposition of cells on a surface", *Biosensors and Bioelectronics*, 2004, 19,1021-1028.
Hemmila, I. et al., "Progress in Lanthanides as Luminescent Probes", *J. Fluoresncence*, 2005, 15, 529-542.
Hertz, H.M. et al., "Standing-wave acoustic trap for nonintrusive positioning of microparticles", *J. Appl. Phys.*, 1995, 78, 4845-4849.
Higashitani, K.O. et al., "Migration of Suspended Particles in Plane Stationary Ultrasonic Field", *Chem. Eng. Sci.*, 1981, 36, 1187-1192.
Hill M. et al., "Modelling in the design of a flow-through ultrasonic separator", *Ultrasonics*, 2000, 38, 662-665.
Hill M. et al., "Modelling of layered resonators for ultrasonic separation", *Ultrasonics*, 2002, 40, 385-392.
Hill, D.H. et al., "Operating Characteristics of Acoustically Driven Filtration Processes for Particulate Suspensions", *Sep. Sci. and Tech.*, 2000, 35, 1363-1375.
Hill, M. et al., "The selection of layer thicknesses to control acoustic radiation forces profiles in layered resonators", *J. Acoust. Soc. Am.*, 2003, 114(5), 2654-2661.
Hirschfeld, T. et al., "Fluorescence Background Discrimination by Prebleaching", *J. Histochem. and Cytochem.*, 1979, 27, 96-101.
Holmes, D. et al., "High throughput particle analysis: Combining dielectrophoretic particle focussing with confocal optical detection", *Biosensors and Bioelectronics*, 2006, 21, 1621-1630.
Holwill, I.L. et al., "The use of ultrasonic standing waves to enhance optical particle sizing equipment", *Ultrasonics*,2000, 38, 650-653.
Huhtinen, P. et al., "Synthesis, Characterization, and Application of Eu(III), Tb(III), Sm (III), and Dy(III) Lanthanide Chelate Nanoparticle Labels", *Anal. Chem.*, 2005, 77, 2643-2648.
Invitrogen, "Fluo-4 NW Calcium Assay Kits (F36205, F36206)", *Product Information*, 2006.
Invitrogen, "Fluorophore selection guide for flow cytometry", *Cellular Analysis*, 2007.
Johnston, P.A. et al., "Cellular platforms for HTS: three case studies", *DDT*, 2002, 7, 353-363.
Jonsson, H. et al., "Particle separation using ultrasound can be used with human shed mediastinal blodd", *Perfusion*, 2005, 20, 39-43.
Juarez, J.A. et al., "Piezoelectric Transducer for Air-Borne Ultrasound", *Acustica*, 1973, 29, 234-239.
Kaduchak, G. et al., "E6 diffraction catastrophe of the primary rainbow of oblate water drops: observations with white-light and laser illumination", *Applied Optics*, 1994, 33, 4691-4696.

Kaduchak, G. et al., "Hyperbolic umbilic and E6 diffraction catastrophes associated with the secondary rainbow of oblate water drops: observations with laser illumination", *Applied Optics*, 1994, 33, 4697-4701.
Kapishnikov, S. et al., "Continuous particle size separation and size sorting using ultrasound in a microchannel", *J. Stat. Mech.*, 2006, 1-13.
Karumanchi, R.S. et al., "Field-assisted extraction of cells, particles and macromolecules", *TRENDS is Biotech*, 2002, 20, 72-78.
Kaye, P.H. et al., "Spatial light-scattering analysis as a means of characterizing and classifying non-spherical particles", *Meas. Sci. Technol.*,1998, 9, 141-149.
Keij, et al.,"Coincidence in High-Speed Flow Cytometry: Models and Measurements," Cytometry 12, Jan. 22, 1991, 398-404.
Kilburn, D.G. et al., "Enhanced Sedimentation of Mammalian Cells following Acoustic Aggregation", *Biotech. and Bioeng.*, 1989, 34, 559-562.
King, L.V. et al., "On the acoustic radiation on spheres", *Proc. R. Soc. A.*, 1933, 147, 212-240.
Kogan, S. et al., "Acoustic concentration of particles in piezoelectric tubes: Theoretical modeling of the effect of cavity shape and symmetry breaking", *J. Acoust. Soc. Am.*, 2004, 116, 1967-1974.
Kozuka, T. et al., "Acoustic Micromanipulation Using a Multi-Electrode Transducer", *7th Inter. Svmp. on Micro Machine and Human Science IEEE*, 1996, 163-170.
Kozuka, T. et al., "Control of a Standing Wave Field Using a Line-Focused Transducer for Two-Dimensional Manipulation of Particles", *Jpn. J. Appl. Phys.*, 1998, 37, 2974-2978.
Kozuka, T. et al., "Micromanipulation Using a Focused Ultrasonic Standing Wave Field", *Electronics and Communications in Japan*, 2000, Part 3, 83(1), 1654-1659.
Kumar, M. et al., "Fractionation of Cell Mixtures Using Acoustic and Laminar Flow Fields", *Biotech. Bioeng.*, 2005, 89, 129-137.
Kundt, A. et al., "Longitudinal vibrations and acoustic figures in cylindrical columns of liquids", *Annalen der Physik und Chemie (Poggendorff's Annalen)*, 1874, 153, 1-12.
Kuznetsova, L.A. et al., "Cavitation buble-driven cell and particle behavior in a ultrasound standing wave", *J. Acoust. Soc. Am.*, 2005, 117, 104-112.
Kuznetsova, L.A. et al., "Microparticle concentration in short path length ultrasonic resonators: Roles of radiation pressure and acoustic streaming", *J. Acoust. Soc. Am.*, 2004, 116, 1956-1966.
Kwiatkowski, C.S. et al., "Resonator frequency shift due to ultrasonically induced microparticle migration in an aqueous suspension: Observations and model for the maximum frequency shift", *J. Acoust. Soc. Am.*, 1998, 103, 3290-3300.
Lakowicz, J.R. et al., "On the Possibility of Long-Wavelength Long-Lifetime High-Quantum-Yield Luminophores", *Analyical Biochemistry*, 2001, 288, 62-75.
Leif, R.C. et al., "Increasing the Luminescence of Lanthanide Complexes", *Cytometry*, 2006, 69A, 767-778.
Leif, R.C. et al., "Markers for Instrumental Evaluation of Cells of the Female Reproductive Tract; Existing and New Markers", in *The Automation of Uterine Cancer Cytology Tutorials of Cytology*, (edited by G.L. Wied. et al.), 1976, 313-344.
Lierke, E.G. et al., "Acoustic Positioning for Space Processing of Materials Science Samples in Mirror Furnaces", *IEEE Ultrasonics Symposium*, 1983, 1129-1139.
Lilliehorn, T. et al., "Trapping of microparticles in the rear field of an ultrasonic transducer", *Ultrasonics*, 2005, 43, 293-303.
Lofstedt, R. et al., "Theory of long wavelength acoustic radiation pressure", *J. Acoust. Soc. Am.*, 1991, 90, 2027-2033.
Loken, M.R. et al., "Cell Discrimination by Multiangle Light Scattering", *Histochem. Cytochem.*, 1976, 24, 284-291.
Loken, M.R. et al., "Identification of Cell Asymmetry and Orientation by Light Scattering", *Histochem. Cytochem.*, 1977, 7, 790-795.
Macey, M.G. et al., "Comparative Study of Five Commercial Reagents for Preparing Normal and Leikaemic Lymphoctyes for Immunophenotypic Analysis by Flow Cytometry", *Cytometry*, 1999, 38,153-160.
Maltsev, V.P. et al., "Scanning flow cytometry for individual particle analysis", *Review of Scientific Instruments*, 2000, 71, 243-255.

(56) References Cited

OTHER PUBLICATIONS

Mandralis, Z. et al., "Enhanced synchronized ultrasonic and flow-field fractionation of suspensions", *Ultrasonics*, 1994, 32, 113-121.

Mandralis, Z. et al., "Transient Response of Fine Particle Suspensions to Mild Planar Ultrasonic Fields", *Fluid/Particle Separation J.*, 1990, 115-121.

Marston, P.L. et al., "Generalized rainbows and unfolded glories of oblate drops: organization for multiple internal reflection and extension of cusps into Alexander's dark band", *Applied Optics*, 1994, 33, 4702-4713.

Marston, P.L. et al., "Manipulation of Fluid Objects with Acoustic Radiation Pressure", *Ann. N.Y. Acad. Sci.*, 2004, 1027, 414-434.

Marston, P.L., "Tensile Strength and Visible Ultrasonic Cavitation of Superfluid 4He*," Journal of Low Temperature Physics, 25(3/4), Mar. 5, 1976, 383-407.

Marston, P.L. et al., "Resonances, Radiation Pressure, and Optical Scattering Phenomena of Drops and Bubbles", *Proceedings of the Second International Colloquium on Drops and Bubbles, Jet Prop. Lab. Pub 82-7* Pasadena, CA, 1982, 166-174.

Martin, K.M. et al., "Acoustic filtration and sedimentation of soot particles", *Experiments in Fluids*, 1997, 23, 483-488.

Masudo, T. et al., "Particle Characterization and Separation by a Coupled Acoustic-Gravity Field", *Analytical Chemistry* 2001, 73, 3467-3471.

Mathies, R.A. et al., "Optimization of High-Sensitivity Fluorescence Detection", *Anal. Chem.*, 1990, 62, 1786-1791.

Mazumdar, M.K. et al., "Spart Analyzer: Its Application to Aerodynamic Size Distribution Measurement", *J. Aerosol Sci.*, 1979, 10, 561-569.

Mazumdar, M.K. et al., "Single particle aerodynamic relaxation time analyzer", *Rev. Sci. Instrum.*, 1977, 48, 622-624.

McCartin, B.J., "A Numerical Procedure for 2D Acoustic Waveguides with Heated Walls", http://flux.aps.org/meetings/YR99/OSS99/abs/S700004.html, 1999.

Meindersma, G.W. et al., "Separation of a biocatalyst with ultrafiltration or filtration after bioconversion", *J. Membrane Sci.*, 1997, 125, 333-349.

Morgan, J. et al., "Manipulation of in vitro toxicant sensors in an ultrasonic standing wave", *Toxicology in Vitro*, 2004, 18, 115-120.

Mullaney, P.F, et al., "The Small Angle Light Scattering of Biological Cells", *Biophys. J.*, 1970, 10, 764-772.

Neild, A., "A micro-particle positioning technique combining an ultrasound manipulator and a microgripper," *J. Micromechanical Microengineering*, 2006, 16, 1562-1570.

Neild, A. et al., "Design, modeling and characterization of microfluidic devices for ultrasonic manipulation", *Sensors and Actuators B: Chemical* , Feb. 20, 2007, 121(2).

Neukammer, J. et al., "Angular distribution of light scattered by single biological cells and oriented particle agglomerates", *Appl. Opt.*, 2003, 42, 6388-6397.

Nilsson, A. et al., "Acoustic control of suspended particles in micro fluidic chips", *Lab Chip*, 2004, 4, 131-135.

Nolan et al., "Suspension Array Technology: New Tools fro Gene and Protein Analysis", *Cell and Molecular Biology*, 2001, 47, 1241-1256.

Nowotny, H. et al., "Layered piezoelectric resonators with an arbitrary number electrodes (general one-dimensional treatment)", *J. Acoust. Soc. Am.*, 1991, 90, 1238-1245.

Otaki, M. et al., "Virus Removal in a Membrane Separation Process", *Water Sci. and Tech.*, 1998 37, 107-116.

Pangu, G.D. et al., "Acoustically aided separation of oil droplets from aqueous emulsions", *Chem. Eng. Sci.*, 2004, 59, 3183-3193.

Petersson et al., "Separation of Lipids from Blood Utilizing Ultrasonic Standing Waves in Microfluidic Channels," *Analyst*, 2004, 129, 938-943.

Petersson, F., "Particle Flow Switch Utilizing Ultrasonic Particle Switching in Microfluidic Channels", *7th International Conf on Miniaturizing Chem and Biochem Analysis Systems*, 2003, 879-882.

Petersson, F. et al., "Continuous separation of lipid particles from erythrocytes by means of laminar flow and acoustic standing wave forces", *Lab Chip*, 2005, 5, 20-22.

Petersson, F. et al., "Carrier Medium Exchange through Ultrasonic Particle Switching in Microfluidic Channels", *Anal. Chem.*, 2005, 77, 1216-1221.

Petersson, F. et al., "Free Flow Acoustophoresis: Microfluidic-Based Mode of Particle and Cell Separation", *Anal. Chem.*, 2007 79, 5117-5123.

Pregibon, D.C. et al., "Multifunctional Encoded Particles for High-Throughput Biomolecule Analysis", *Science*, 2007, 315, 1393-1396.

Princen, K. et al., "Evaluation of SDF-1/CXCR4-Induced Ca2+Signaling by Fluorometric Imaging Plate Reader (FLIPR) and Flow Cytometry", *Cytometry*, 2003, 51A, 35-45.

Pui, P.W. et al., "Batch and Semicontinuous Aggregattion and Sedimentation of Hybridoma Cells by Acoustic Resonance Fields", *Biotechnol. Prog.*, 1995, 11, 146-152.

Rama Rao, G.V. et al., "Monodisperse Mesoporous Silica Microspheres Formed by Evaporation-Induced Self Assembly of Surfacant Templates in Aerosols", *Advanced Materials*, 2002, 18,1301-1304.

Rens, W. et al., "A Novel Nouel for More Efficient Sperm Orientation to Improve Sorting Efficiency of X and Y Chromosome-Bearing Sperm", *Cytometry*, 1998, 33, 476-481.

Ricks, D.C. et al., "A numerically stable global matrix method for cylindrically layered shells excited by ring forces", *J. Acoust. Soc. Am.*, 1994, 95, 3339-3349.

Rouleau, F. et al., "Electromagnetic scattering by compact clusters of spheres", *Astron. Astrophys*, 1996, 310, 686-698.

Rudnick, J. et al., "Oscillational instabilities in single-mode acoustic levitators", *J. Acoust. Soc. Am.*, 1990, 87, 81-92.

Saito, M. et al., "Microorganism manipulation and microparticle arrangement by the use of ultrasonic standing waves", *SPIE*, 2001, 4590, 26-37.

Saito, M. et al., "Ultrasonic manipulation of locomotive microorganisms and evaluation of their activity", *J. App. Physics*, 2002, 92, 7581-7586.

Saito, M. et al., "Ultrasonic trapping of paramecia and estimation of their locomotive force", *Appl. Phys. Lett*,1997, 71,1909-1911.

Saito, M. et al., "Ultrasonic waves for fabricating lattice structure in composite materials", *SPIE*, 1999, 3786, 179-190.

Saito, M. et al., "Quantum mechanical representation of acoustic streaming and acoustic radiation pressure", *Physical Review*, 2001, E64, 026311-1-026311-5.

Samiotaki, M. et al., "Seven-Color Time-Resolved Fluorescence Hybridization Analysis of Human Papilloma Virus Types", *Analytical Biochem.*, 1997, 253, 156-161.

Schmid, M. et al., "A computer-controlled system for the measurement of complete admittance spectra of piezoelectric resonators", *Meas. Sci. Technol.*, 1990, 1, 970-975.

Schoell, W.M. et al., "Separation of Sperm and Vaginal Cells with Flow Cytometry for DNA Typing After Sexual Assault", *Obstetrics and Gynecolony*, 1999, 94, 623-627.

Semianov, K.A. et al., "Measurement of Mammalian Erythrocyte Indices from Light Scattering with Scaning Flow Cytometer", *Proc. SPIE*, 2003, 5141,106-113.

Sethu, P. et al., "Continuous Flow Microfluidic Device for Rapid Erythrocyte Lysis", *Anal. Chem.*, 2004, 76, 6247-6253.

Shapiro, H.M. et al., *Practical Flow Cytometry*, Hoboken, NJ, John Wiley & Sons. Inc., 2005, 9-13.

Shvalov, A.N. et al., "Individual *Escherichia coli* Cells Studied from Light Scattering with the Scanning Flow Cytometer", *Cytometry*, 2000, 41, 41-45.

Shvalov, A.N. et al., "Light -scattering properties of individual erythrocytes", *Applied Optics*, 1999, 38, 230-235.

Simpson, H.J. et al., "Ultrasonic four-wave mixing mediated by an aqueous suspension of microspheres: Theoretical steady-state properties", *J. Acoust. Soc. Am.*, 1995, 98, 1731-1741.

Skudrzyk, E. et al., "Die Grundlagen der Akustic", *Sprinaer Verlaa. Wien*, 1954, 202-205 and 807-825.

(56) References Cited

OTHER PUBLICATIONS

Slomkowski, S. et al., "New Types of Microspheres and Microsphere-related Materials for Medical Diagnostics", *Polymers for Advanced Technologies*, 2002, 13, 906-918.

Sobanski, M.A. et al., "Sub-micron particle manipulation in an ultrasonic standing wave: Applications in detection of clinically important biomolecules", *Bioseparation*, 2001, 9, 351-357.

Steinkamp, J.A., "A Differential Amplifier Circuit for Reducing Noise in Axial Light Loss Measurements", *Cyometry*, 1983, 4, 83-87.

Steinkamp, J.A. et al., "Dual-Laser, Differential Fluorescence Correction Method for Reducing Cellular Background Autofluorescence", *Cytometry*, 1986, 7, 566-574.

Steinkamp, J.A. et al., "Enhanced Immunofluorescence Measurement Resolution of Surface Antigens on Highly Autofluorescent, Glutaraldehyde-Fixed Cells Analyzed by Phase-Sensitive Flow Cytometry", *Cytometry*, 1999, 37, 275-283.

Stewart, C.C. et al., "Resolving Leukocytes Using Axial Light Loss", *Cytometry*, 1989, 10, 426-432.

Stoffel, C.L. et al., "Data Analysis for a Dual Analysis for a Dual-Channel Virus Counter", *Analytical Chemistry*, 2005, 77, 2243-2246.

Stoffel, C.L. et al., "Design and Characterization of a Compact Dual Channel Virus Counter", *Cytometry*, 2005, Part A 65A, 140-147.

Stovel, R.T. et al., "A Means for Orienting Flat Cells in Flow Systems", *Biophys J.*, 1978, 23, 1-5.

Takeuchi, M. et al., "Ultrasonic Micromanipulation of Small Particles in Liquid", *Jpn J. Appl. Phys.*, 1994, 33, 3045-3047.

Takeuchi, J. et al., "Ultrasonic Micromanipulator Using Visual Feedback", *Jpn J. Appl. Phys.*, 1996, 35, 3244-3247.

Thiessen, D.B. et al., "Principles of some Acoustical, Electrical, and Optical Manipulation Methods with Applications to Drops, Bubbles, and Capillary Bridges", *ASME Fluids Eng. Div. Publ. FED*, 1998.

Thiessen, D.B. et al., "Some Responses of Small Diffusion Flames to Ultrasonic Radiation", *NASA*, 2003, 321-324.

Tolt, T.L. et al., "Separation devices based on forced coincidence response of fluid-filled pipes", *J. Acoust. Soc. Am.*, 1992, 91, 3152-3156.

Tolt, T.L. et al., "Separation of Dispersed Phases from Liquids in Acoustically Driven Chambers", *Chem. Eng. Science*, 1993, 48, 527-540.

Townsend, R.J. et al., "Modelling of particle paths passing through an ultrasonic standing wave", *Ultrasonics*, 2004, 42, 319-324.

Trihn, E.H. et al., "Experimental study of streaming flows associated with ultrasonic levitators", *Phys. Fluids*, 1994, 6, 3567-3579.

Trinh, E.H. et al., "Compact acoustic levitation device for studies in fluid dynamics and material science in the laboratory and microgravity", *Rev. Sci. Instrum.*, 1985, 56, 2059-2065.

Tuckermann, R. et al., "Trapping of heavy gases in stationary ultrasonic fields", *Chem. Phys. Ltrs.*, 2002, 363, 349-354.

Tung, Yi-C. et al., "PDMS-based opto-fluidic micro flow cytometer with two-color, multi-angle fluorescence detection capability using PIN photodiodes", *Sensors and Actuators*, 2004, 98, 356-367.

Tyson, D.S. et al., "Ruthenium (II) complex with a notably long excited state lifetime", *The Royal Society of Chemistry*, 2000, 2355-2356.

Vainshtein, P. et al., "On the Drift of Aerosol Particles in Sonic Fields", *J. Aerosol Sci.*, 1992, 23, 631-637.

Vainshtein, P. et al., "The effect of centreline particle concentration in a wave tube", *J. Fluid Mech.*, 1996, 306, 31-42.

Van Hee, P. et al., "Strategy for Selection of Methods for Separation of Bioparticles From Particle Mixtures", *Biotech. Bioeng.*, 2006, 94, 689-709.

Verpoorte, E. et al., "Beads and chips: new recipes for analysis—Elisabeth Verpoorte reviews particle handling in microchannels", *Lab Chip*, 2003, 3, 60N-68N.

Visuri, S.V. et al., "Microfluidic tolls for biological sample preparation", *Poster 1423, 2nd Annual International IEEE-EMBS Special Topic Cofnerence on Microtechnologies in Medicine & Biology*, May 2-24, 2002, 556-559.

Wang, Z. et al., "Retention and Viability Characteristics of Mammalian Cells in an Acoustically Driven Polymer Mesh", *Biotechnol. Prog.*, 2004, 20, 384-387.

Ward, M. et al., "Manipulation of Immunomagnetic Targets in Microfluidic Channel Flow", *Dissertation*, 2005, 1-205.

Weiser, M.A. et al., "Interparticle Forces on Red Cells in a Standing Wave Field", *Acustica*, 1984, 56, 114-119.

Weiser, M.A.H. et al., "Extension of acoustic levitation to include the study of micron-size particles in a more compressible host liquid", *J. Acoust. Soc. Am.*, 1982, 71, 1261-1268.

Whitworth, G. et al., "Particle column formation in a stationary ultrasonic field", *J. Acoust. Soc. Am.*, 1992, 91, 79-85.

Whitworth, G. et al., "Transport and harvesting of suspended particles using modulated ultrasound", *Ultrasonics*, 1991, 29, 439-444.

Wu, Y. et al., "Diazo Coupling Method for Covalent Attachment of Proteins to Solid Substrates", *Bioconjugate Chem.*, 2006, 17, 359-365.

Yagi, et al., "Flow Cytometry to Evaluate Theileria Sergenti Parasitemia Using the Florescent Nucleic Acid Stain SYTO16," *Cytometry*, 2000, 41, 223-225.

Yamakoshi, Y. et al., "Micro particle trapping by opposite phases ultrasonic travelling waves", *Ultrasonics*, 1998, 36, 873-878.

Yasuda, K. et al., "Concentration and Fractionation of Small Particles in Liquid by Ultrasound", *Jpn J. Appl. Phys.*, 1995, 34, 2715-2720.

Yasuda, K. et al., "Deoxyribonucleic acid concentration using acoustic radiation force", *J. Acoust. Soc. Am.*, 1996, 99, 1248-1251.

Yasuda, K. et al., "Non-destructive, non-contact handling method for biomaterials in micro-chamber by ultrasound", *Sensors and Actuators*, 2000, 64, 128-135.

Yasuda, K. et al., "Particle separation using acoustic radiation force and elecrostatic force", *J. Acoust. Soc. Am.*, 1996, 99, 1965-1970.

Yasuda, K. et al., "Blood Concentration by Superposition of Higher Harmonics of Ultrasound", *Jpn. J. Appl. Phys.*, 1997, 36, 3130-3135.

Yasuda, K. et al., "Using acousitc radiation force as a concentration method for erythrocytes", *J. Acoust. Soc. Am.*, 1997, 102, 642-645.

Ye, C-H. et at., "Preparation of three terbium complexes with paminobenzoic acid and investigation of crystal structure influence on luminescence property", *Journal of Solid State Chemistry*, 2004, 177, 3735-3742.

Yosioka, K. et al., "Acoustic Radiation Pressure on a Comressible Sphere", *Acustica*, 1955, 5, 167-173.

Yuan, J. et al., "Lanthanide-based luminescence probes and time-resolved luminescence bioassays", *Trends in Analytical Chemistry*, 2006, 25, 490-500.

Yurkin, M.A. et al., "Experimental and theoretical study of light scattering by individual mature red blook cells by use of scanning flow cytometry and a discrete dipole approximation", *Applied Optics*, 2005, 44, 5249-5256.

EPO Application No. EP 08733084: Extended European Search Report dated Mar. 24, 2010.

Response to Mar. 24, 2010 Extended European Search Report in European Application No. 08733084.1 filed Jun. 16, 2010.

International Application No. PCT/US05/26524: International Search Report dated Oct. 3, 2006.

International Application No. PCT/US08/87579: International Search Report dated Feb. 9, 2009.

International Application No. PCT/US08/87579, Written Opinion dated Feb. 9, 2009.

International Application No. PCT/US2008/059181: International Search Report dated Jul. 25, 2008.

International Application No. PCT/US2009/031154: International Search Report dated Jul. 8, 2009.

U.S. Appl. No. 11/982,042: Restriction Requirement dated Nov. 30, 2009.

U.S. Appl. No. 11/982,042: Non-Final Office Action dated Jun. 10, 2010.

(56) References Cited

OTHER PUBLICATIONS

U.S. Appl. No. 11/982,042: Final Office Action dated Sep. 24, 2010.
U.S. Appl. No. 11/982,042: Non-Final Office Action dated Mar. 4, 2011.
U.S. Appl. No. 11/982,042: Final Office Action dated Oct. 17, 2011.
U.S. Appl. No. 11/593,312: Non-Final Office Action dated Oct. 16, 2008.
U.S. Appl. No. 11/593,312: Final Office Action dated May 13, 2009.
U.S. Appl. No. 11/593,312: Non-Final Office Action dated Oct. 23, 2009.
U.S. Appl. No. 11/593,312: Final Rejection dated Apr. 5, 2010.
U.S. Appl. No. 11/593,312: Notice of Allowance dated Jul. 6, 2010.
U.S. Appl. No. 11/593,312: Notice of Allowance dated Sep. 16, 2010.
U.S. Appl. No. 11/784,928: Restriction Requirement dated Jul. 1, 2009.
U.S. Appl. No. 11/784,928: Non-Final Office Action dated Dec. 30, 2009.
U.S. Appl. No. 11/784,928: Final Rejection dated Jul. 7, 2010.
U.S. Appl. No. 11/784,928: Notice of Allowance dated Dec. 13, 2010.
U.S. Appl. No. 11/784,936: Non-Final Office Action dated Apr. 3, 2008.
U.S. Appl. No. 11/784,936: Final Office Action dated Dec. 31, 2008.
U.S. Appl. No. 11/784,936: Non-Final Office Action dated Jun. 24, 2009.
U.S. Appl. No. 11/784,936: Notice of Allowance dated Feb. 22, 2010.
U.S. Appl. No. 11/784,936: Notice of Allowance dated May 28, 2010.
U.S. Appl. No. 11/784,936: Notice of Allowance dated Sep. 16, 2010.
U.S. Appl. No. 12/283,461: Restriction Requirement dated Jun. 28, 2010.
U.S. Appl. No. 12/283,461: Non-Final Office Action dated Sep. 28, 2010.
U.S. Appl. No. 12/283,461: Final Office Action dated Apr. 5, 2011.
U.S. Appl. No. 12/283,461: Non-Final Office Action dated Sep. 26, 2011.
U.S. Appl. No. 12/903,003: Non-Final Office Action dated Nov. 15, 2010.
U.S. Appl. No. 12/903,003: Final Office Action dated Jun. 23, 2011.
U.S. Appl. No. 12/903,003: Non-Final Office Action dated Oct. 24, 2011.
U.S. Appl. No. 12/283,491: Restriction Requirement dated Jun. 25, 2010.
U.S. Appl. No. 12/283,491: Non-Final Office Action dated Sep. 27, 2010.
U.S. Appl. No. 12/283,491: Final Office Action dated Apr. 5, 2011.
U.S. Appl. No. 12/283,491: Non-Final Office Action dated Sep. 27, 2011.
U.S. Appl. No. 12/283,491: Ex parte Quayle Action dated Mar. 29, 2012.
U.S. Appl. No. 12/283,491: Notice of Allowance dated May 25, 2012.
U.S. Appl. No. 12/283,461: Ex parte Quayle Action dated Mar. 29, 2012.
U.S. Appl. No. 12/283,461: Notice of Allowance dated May 31, 2012.
U.S. Appl. No. 12/903,003: Final Office Action dated Feb. 6, 2012.
U.S. Appl. No. 12/903,003: Non-Final Office Action dated Jun. 19, 2012.
U.S. Appl. No. 12/903,003: Final Office Action dated Oct. 24, 2012.
U.S. Appl. No. 12/903,042: Non-Final Office Action dated May 11, 2012.
U.S. Appl. No. 12/903,042: Non-Final Office Action dated Nov. 15, 2012.
U.S. Appl. No. 13/295,934: Non-Final Office Action dated Oct. 9, 2012.
U.S. Appl. No. 12/903,003: Non-Final Office Action dated Feb. 13, 2013.
U.S. Appl. No. 12/903,042: Non-Final Office Action dated Sep. 18, 2013.
U.S. Appl. No. 13/618,237: Restriction Requirement dated Sep. 3, 2013.
Anderson, M.J. et al., "Use of Acoustic Radiation Pressure to Concentrate Small Particles in an Air Flow," 2002 IEEE Ultrasonics Symposium, Jan. 1, 2002, 481-484.
U.S. Appl. No. 12/903,003: Notice of Allowance dated Jun. 5, 2013.

* cited by examiner

PARTICLE ANALYSIS IN AN ACOUSTIC CYTOMETER

CROSS REFERENCE TO RELATED APPLICATIONS

This application is a continuation of U.S. patent application Ser. No. 12/283,491, entitled "Particle Analysis in an Acoustic Cytometer," filed Sep. 11, 2008, which application claims the benefit of U.S. Provisional Patent Application Ser. No. 61/008,422, entitled "Particle Analysis in an Acoustic Cytometer," filed Dec. 19, 2007. All of the foregoing applications are incorporated herein by reference in their entireties for all purposes.

TECHNICAL FIELD

Embodiments of the present invention relate to acoustic cytometry and more specifically to particle analysis in an acoustic cytometer.

BACKGROUND

It was realized early in the development of flow cytometry that the angular dependence of the light scattering intensity from a particle contains a wealth of information related to a particle's intrinsic and extrinsic properties. For example, Mullaney, et al. experimentally demonstrated the use of forward light scatter (0.5-2 degrees) for cell size estimation. In the same time period, it was also realized that cell orientation relative to the incident light beam can introduce artifacts that affect population resolution and instrument sensitivity for particles that do not possess axial symmetry parallel to the flow direction. Loken et al. showed that nonspherical particles in the form of fixed chicken erythrocytes yield a bimodal scattering distribution that is related to rim-on or face-on illumination of the disk-cell structure. Particle orientation dependent scattering effects due to asymmetries that are apparent in the complex geometrical shape of sperm cells have also been demonstrated. Several researchers have suggested passive solutions to orienting particles by shaping the sample nozzle to introduce asymmetries into the velocity flow field of the hydrodynamic sheath system. It has been shown that the most critical aspect in efficient X and Y sperm discrimination in flow cytometric sorting is the orientation of the sperm in the optical scattering plane. Recently, novel nozzle geometries have demonstrated proper orientation of up 60% of the sperm heads in the optical scattering plane at analysis rates near 2000 particles/s dramatically affecting the sorting efficiency. Other researchers have addressed particle asymmetries by collecting data over a large array of scattering angles using scanning flow cytometry (SFC) at the cost of lower particle analysis rates (approximately 400 particles/s). Systems have demonstrated continuous angular scattering data spanning 70 degrees but the data is taken relative to an arbitrary particle orientation that results in large variations of the collected angular spectra for asymmetric particles.

One of the earliest large-scale demonstrations of separating biological cells using acoustic forces was done by Doblhoff, et al. In that system, acoustic radiation pressure was used for selective retention of viable hybridoma cells for the purpose of removing nonviable cells and smaller cellular debris from a 20 liter bioreactor. That system was based on a multi-planar transducer design and demonstrated viable cell retention rates as high as 99.5% with varying results for cellular debris rejection. That early system required high power input (in excess of 15 W) thus necessitating a cooling unit for the drive transducers. More recently, Feke and coworkers developed a novel particle separation strategy that relies on both acoustic radiation pressure and secondary acoustic forces. A high-porosity polyester mesh (pore size two orders of magnitude greater than particle size) in an acoustic standing wave served as a collection matrix whereby particles at nodal locations were trapped within the mesh and secondary acoustic forces formed particle agglomerates and created an attractive force at the mesh surface. In a similar demonstration of retention of hybridoma cells, retention efficiencies of about 95% were achieved with negligible effects on cell viability. This system achieved high cell densities of approximately $1.5 \times 10^{8}$ cells/mL with only hundreds of milliWatts of input power.

SUMMARY

One embodiment of the present invention comprises a method for acoustically manipulating one or more particles. This embodiment preferably includes flowing a fluid containing particles therein, applying acoustic radiation pressure to the fluid and acoustically manipulating the one or more particles, stopping the fluid, and reviewing at least one of the particles. In this embodiment of the present invention reviewing at least one of the particles can include analyzing at least one of the particles, and/or sorting at least one of the particles. The particles can also be flowed through a flow cytometer.

Another embodiment of the present invention comprises a method for acoustically manipulating one or more particles. This embodiment includes flowing a fluid containing particles therein, applying acoustic radiation pressure to the fluid and acoustically manipulating the one or more particles, reversing the direction of flow, and reviewing at least one of the particles that were reversed in the flow. In this embodiment, reviewing the particles can comprise analyzing at least one of the particles and/or sorting at least one of the particles. This embodiment can also include flowing the fluid through a flow cytometer.

Yet another embodiment of the present invention comprises a method for acoustically aligning and orienting particles in a flow stream of a particle analyzer comprising flowing particles through the flow stream, subjecting the particles to an acoustic radiation pressure, acoustically aligning the particles in the flow stream of the particle analyzer, and acoustically orienting the particles in the flow stream of the particle analyzer. In this embodiment, the particle analyzer can be a flow cytometer. This method can also include a non-axisymmetric field wherein the particles are asymmetric. Further, this embodiment optionally comprises selecting a predetermined orientation of the particles, where the orientation is within an optical scattering plane. This embodiment can comprise distinguishing between different types of particles based upon particle asymmetries. This embodiment can further comprise yielding repeatable orientations of particle clusters or sorting particles. The sorting of the particles can include pre-analysis in-line separating of particles based on size. In addition, this embodiment can align the particles in a polar direction about a flow axis or align the particles in a direction of flow. Still further, this embodiment can optionally comprise fractionating the particles. In this embodiment, the particle can be a red blood cell, a platelet or a sperm.

Another embodiment of the present invention comprises a method for analyzing particles in a particle analyzer. This method preferably comprises flowing particles in a flow stream, applying a radial acoustic radiation pressure to the flow stream, acoustically orienting non-axial symmetric particles in the flow stream, transporting the particles through an interrogation point, and analyzing the particles. This embodiment can also include aligning the particles in a flow stream with either an acoustic field or a hydrodynamic focus. This method also preferably comprises concentrating the particles in the flow stream.

Still another embodiment of the present invention comprises a method of analyzing one or more particles in a flow stream. This embodiment preferably comprises labeling the particles with a lanthanide, flowing the particles in the flow stream, applying acoustic radiation pressure to the flow stream to maintain particle focus regardless of flow rate, and analyzing the particles with the lanthanide. This embodiment can also include stopping and/or reversing the flow stream.

A further embodiment of the present invention comprises a method for sorting particles by size. This method preferably comprises flowing particles in the flow stream, applying radial acoustic radiation pressure to the flow stream, and acoustically sorting and separating the particles by size. This method also preferably comprises transporting larger particles of the separated particles into a flow cytometer and analyzing the larger particles. The transporting step of this embodiment preferably transports the larger dependent particles to a central axis of the flow stream. This embodiment also preferably comprises in-line sorting.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF ILLUSTRATIVE EMBODIMENTS

As used herein "a" means one or more.

As used herein "capillary" means a flow channel or chamber having a shape selected from rectangular, elliptical, oblate circular, round, octagonal, heptagonal, hexagonal, pentagonal, and triagonal.

In one embodiment of the present invention, acoustic radiation pressure preferably focuses particles to the center of a capillary. This embodiment enables fundamental changes in the way single cells or particles can be either analyzed or processed in a flow stream. This sample delivery embodiment expands the analysis capabilities of flow cytometry by improved analysis and/or preanalysis sample preparation and purification.

Figure 1:
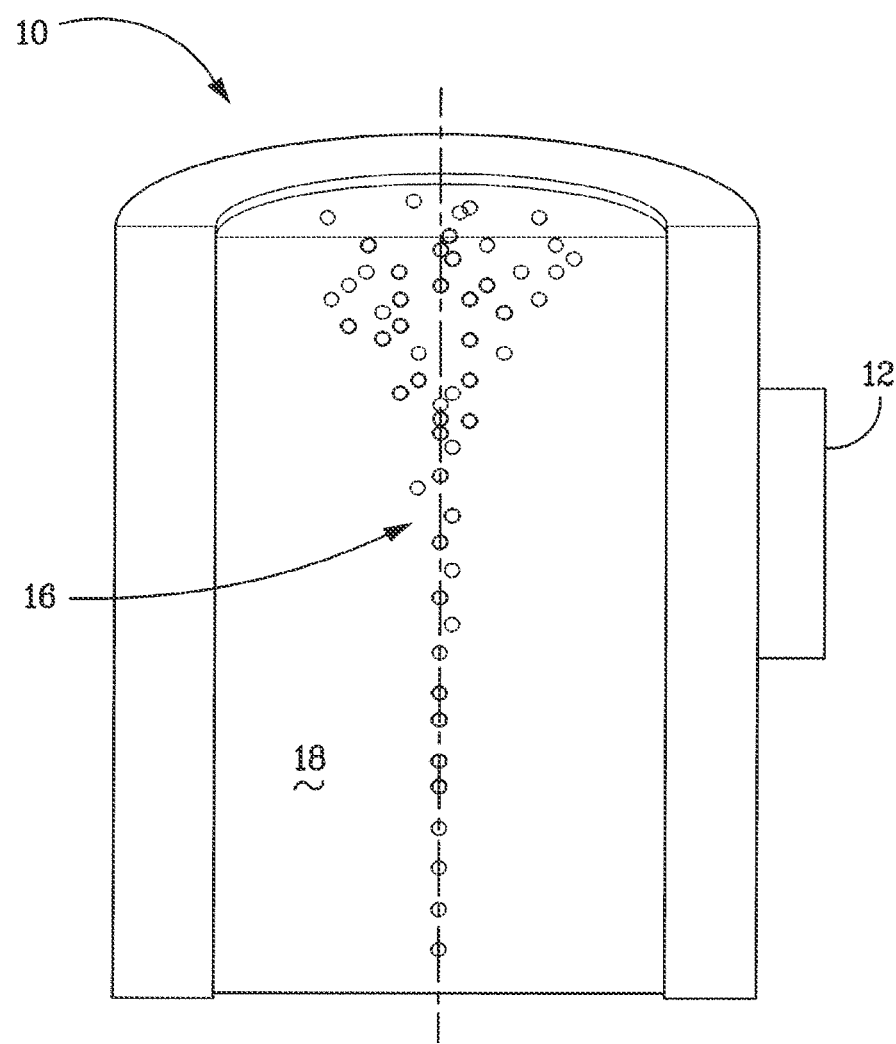
FIG. 1 is an embodiment of the present invention illustrating a line drive capillary where particles are acoustically focused to the central axis of the capillary.

A non-limiting embodiment of an acoustic particle focusing device is illustrated in FIG. 1. This device preferably comprises acoustically driven capillary 10 where an acoustic particle trap oriented parallel to the flow direction comprises line source 12 and fluid 18 with particles/cells 16. This embodiment enables removal of high-velocity sheath flow associated with hydrodynamic focusing and allows extended particle transit times within the optical interrogation region while maintaining a high particle analysis rate due to an inherent in-line particle concentration effect. Additionally acoustic focusing of the particle stream provides the ability to stop and reverse the flow direction without defocusing the particle stream while maintaining particle registration. The increased particle transit times provide an opportunity for high-sensitivity optical measurements that use low-power light sources and less sensitive optical components. Control of flow direction and rate allows for reanalysis of targets of high significance thereby minimizing uncertainties in the scattering data associated with system level fluctuations.

An additional property of an acoustically driven flow chamber is a non-axisymmetric force field that is created within the flow stream. Force asymmetries within the flow chamber orient nonspherical cells or particles such that consistent scattering signatures, that are not possible with standard hydrodynamic flow systems, are produced by positioning asymmetric particles in a predetermined orientation within the optical scattering plane. In this embodiment, optical scattering data associated with specific particle orientation can, for example, distinguish between different types of bacteria based upon particle asymmetries and improve analysis and sorting of irregular cell types such as RBC's and sperm cells. The asymmetric force field also yields repeatable orientations of particle clusters that are formed from the coalescence of multiple microspheres or cells (e.g. 'dumbbell' shapes from agglutination of two particles). Discrimination of particle clusters can be made easier by pulse shape analysis and angular scattering interpretation due to the unique induced orientation of the cluster relative to the scattering plane (e.g. central axis of the 'dumbbell' always parallel to the flow axis).

An acoustically line-driven capillary embodiment of the present invention brings new modes of particle and cell analysis to the detection system of a flow cytometer, and is also employed in particle or cell separations for in-line sample preparation. A primary advantage of acoustic radiation pressure is that it can be used in fairly large chambers with high volume throughput. The acoustic field acts similarly on most biological particles and is thus inherently nonspecific whereby most biological particles are transported to the same spatial location. The magnitude of the field, however, is highly size dependant and makes acoustic radiation pressure an excellent candidate in applications that require high throughput, pre-analysis in-line separating of particles based upon size e.g. sperm from vaginal cells in forensic analysis, virus from bacteria or intact cells from cellular debris. In the description above, a line-driven capillary with a cylindrical geometry is used as the acoustic focusing device, but general geometry (square, rectangular, elliptical, oblate circular, etc.) devices that employ acoustic radiation pressure to position the particles can be used in applications of particle separation, debris rejection, particle alignment, and sample purification.

Acoustic Radiation Pressure

The force on a particle resulting from acoustic radiation Pressure depends upon frequency of excitation, pressure amplitude within the medium, and the density/compressibility contrast between the particle and the host medium. Within an acoustic standing wave, it is a time-averaged drift force which transports the particles to a nodal or an anti-nodal position. The expression for the acoustic radiation force potential U on a spherical particle in an acoustic standing wave is given by:

$$U = \frac{4}{3}\pi a^2 \left[ \left( \beta_o \frac{\langle p^2 \rangle}{2} \right) f_1 - \frac{3}{2} \left( \frac{\rho_o \langle v^2 \rangle}{2} \right) f_2 \right]$$

Here, —a is the particle radius, $\beta_o$ is the compressibility of the surrounding fluid, and $\rho_o$ is the density of the surrounding fluid. The pressure and velocity of the acoustic field in the absence of the particle are described by p and v, respectively, and the brackets correspond to a time-averaged quantity. The terms $f_1$ and $f_2$ are the contrast terms that determine how the mechanical properties of the particle differ from the background medium. They are given by:

$$f_1 = 1 - \frac{\beta_p}{\beta_o}$$

$$f_2 = \frac{2(\rho_p - \rho_o)}{(2\rho_p - \rho_o)}$$

The subscript p corresponds to intrinsic properties of the particle. The force F acting on a particle is related to the gradient of the force potential by:

$$F = -\nabla U$$

Particles are preferably localized at positions where the potential U displays a minimum. (For a circular cross section capillary, a potential minimum is coincident with the axis of the capillary forming the particle trap in FIG. 1 when driven in a dipole type mode. Other modes exist and are advantageous for spatial positioning of particles in locations other than the axis of the capillary for selected applications.)

Acoustic Line-Driven Capillary

Forces resulting from acoustic radiation pressure are preferably an effective means to localize particles in an arrangement similar to hydrodynamic focusing without the need for sheath fluids. The line-driven capillary of the present invention has been proven effective in sheath replacement. (A capillary with a source aperture larger than a line contact can yield similar results. This embodiment has demonstrated acoustically driven capillaries with source apertures that have an extended contact length along the circumference of the capillary that spans more than about 45 degrees.) It is constructed from a capillary that is driven by a piezoceramic source in contact with its outer wall. Vibration of the structure creates a localized pressure node along the central axis where an axial particle trap is formed. A diagram of this device is given in FIG. 1. Particles in a dilute suspension enter the device from the top and experience a radial force that transports them to the pressure node as they flow through the system. In an embodiment of the present invention, the particles contained in a sample are simultaneously concentrated and aligned in single file as they are then transported through the interrogation laser. The particles are transported through the interrogation laser via various transport devices, including but not limited to, a pump and/or one or more valves.

Implementation of acoustic particle focusing preferably allows new flow cytometry techniques and methods to evolve due to fundamental changes in the way particles are positioned within the sample cell. Concentric flow streams with different flow velocities are not required as with conventional hydrodynamically sheath-focused systems. Acoustically focused sample streams can be stopped, slowed, reversed or any combination thereof without degrading alignment of the particle stream within the flow chamber. The increased residence time within the acoustic field produces a Stream of particles whose focus is actually improved. Additionally, the flow can be reversed with no adverse effect on particle alignment within the flow chamber allowing rare targets to be repeat analyzed or stopped for extended analysis such as spectral decomposition of the scattered/fluorescence signature.

One of the unique flow capabilities of the present invention is the ability to select the sample delivery rate. By slowing cell/particle transit times (approximately 20-100 times slower than conventional systems) higher sensitivity optical measurements and measurements of photonic events that require longer interrogation times such as luminescence are possible.

Particle Orientation in a Standing Acoustic Wave Field

Figure 2A:
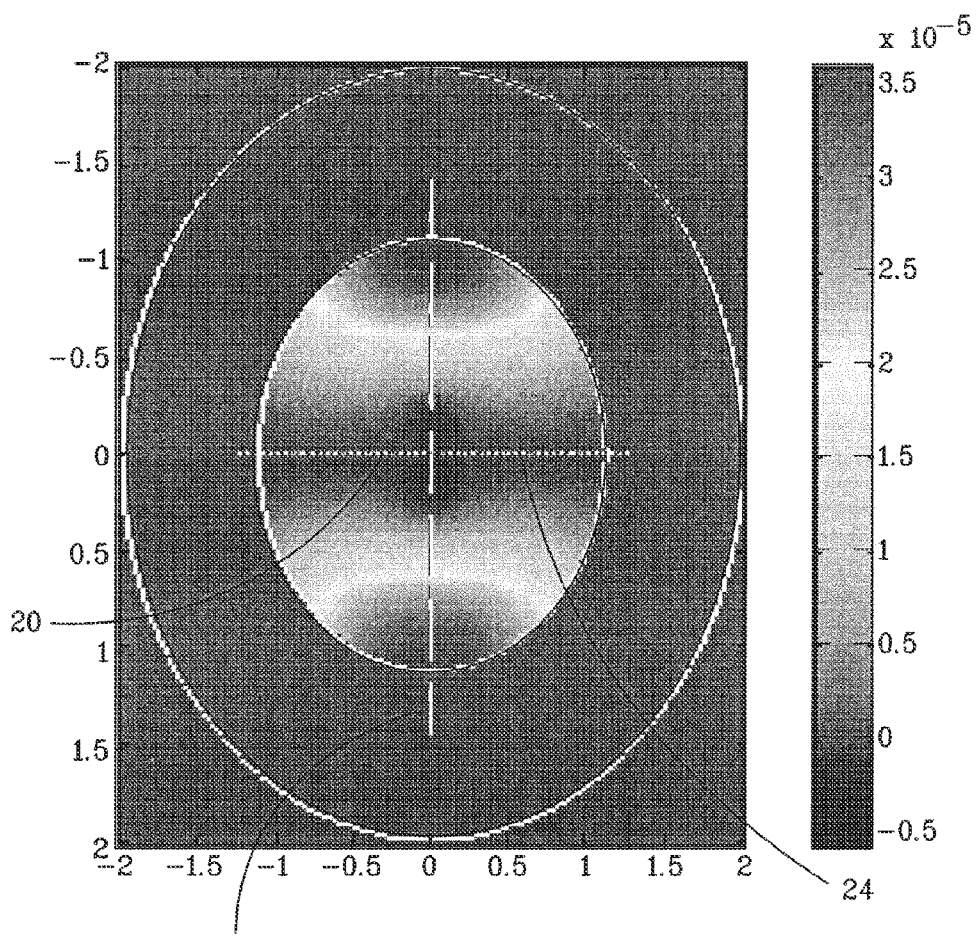
FIG. 2A is a density plot of acoustic force potential in the cross section of a circular capillary driven by a line source according to one embodiment of the present invention.
Figure 2B:
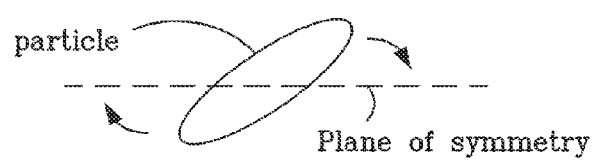
FIG. 2B illustrates an induced particle rotation to lie in a stable force equilibrium plane according to one embodiment of the present invention.

A known orientation of a particle as it passes through the interrogation region enables light scatter/fluorescence measurements that provide significant insight into cellular structure and intrinsic optical properties. The removal of several degrees of rotational freedom proves an invaluable tool to flow cytometry by increasing the value of current light scatter measurements by calibrating them to a specific orientation of a cell/particle and allowing reasonable consideration of new scatter angles as measured parameters. The acoustic line-driven capillary of the present invention (or other methods to introduce acoustic radiation pressure into the flow cell) is an active means to rotate and align particles in both the direction of flow and in polar directions about the flow axis to yield angular calibrated scattering data for particles that are non-spherical. The force experienced by a particle in an acoustically driven tube is inherently non-axisymmetric within the cross section of the flow plane. The acoustic force distribution is dipolar in nature for particle focusing to the tube axis yielding force reflection symmetries within the plane. Calculations of the acoustic force potential U for a particle in a line driven tube in a dipole type mode as one example of this method are shown in FIG. 2(a) where the acoustic force $F_u$ can be obtained by $$F = -\nabla U$$

where the flow direction is into the page. The in-plane force potential possesses reflection symmetry about two planes that intersect the central axis. The first plane of symmetry intersects central axis 20 and line drive 22 and the second plane of symmetry lies perpendicular to the first. Though two symmetry planes exist within the displayed two-dimensional acoustic force potential, only one results in stable equilibrium 24 location with respect to particle rotation. All regular particles will rapidly rotate into stable equilibrium 24 under small perturbations within the flow field as shown in FIG. 2(b).

Incorporating a third dimension into the force field calculation (axial component) yields an additional restriction in the rotational freedom of a particle induced by the acoustic force field. Calculations show that rod shaped particles (particles with two equal minor axes and one major axis) will align their major axis with the axis of the capillary. Particles with bilateral symmetry, e.g. red blood cells, will align one major axis parallel to the flow axis and the other major axis parallel to the stable symmetry plane denoted by the white dotted line in FIG. 2(a).

Acoustic Separation of Cells and Cellular Debris

For particle transport to occur in an acoustically driven chamber according to one embodiment of the present invention, the acoustic force must be large enough to overcome the Brownian motion of the particles within the suspending medium. The magnitude of the acoustic radiation pressure force experienced by a particle is directly proportional to the particle volume, drive level of the acoustic field, mechanical properties of the medium and particle, and the spatial gradient of the acoustic field. For this reason, (due to a cubic relationship of particle radius) larger particles can be transported in an acoustic field at lower pressure amplitudes and excitation frequencies (smaller gradients) than smaller particles. (This is also true for particles that have a greater relative difference in their mechanical properties relative to the background medium.)

Figure 3:
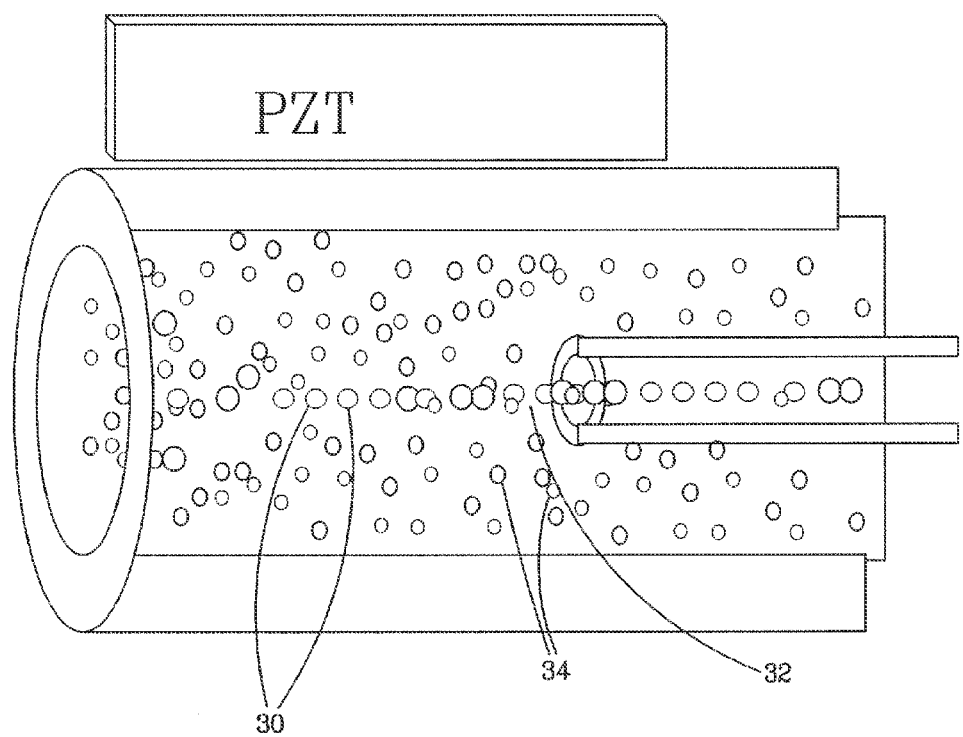
FIG. 3 is an embodiment of the present invention illustrating a line driven acoustic fractionator where large particles are transported to the capillary axis while smaller particles remain unaffected by the acoustic field.

One aspect of one embodiment of an acoustic separation system of the present invention is that it can operate clog-free (no filter) with almost zero pressure drop across the unit. Due to the size dependence inherent in the acoustic radiation force and thermal particle motion, an embodiment of the present invention can separate samples at the front end of a flow stream based upon particle size and mechanical contrast. Acoustic forces are used to purify samples by concentrating analytes of interest at a specified location for selective collection leaving background debris unaffected. Such a system reduces analysis time for samples with high particulate backgrounds on a flow cytometer by greatly reducing the particle count and increasing data quality. For instance, Bossuyt showed that cellular debris within whole blood samples prepared by selected lysis methods can yield scattering events that account for up to 80% of all events in CD45 cell counting on a flow cytometer. Macey noted that certain whole blood lysis methods for preparing lymphocytes for flow cytometry analysis can result in poor forward and side scatter resolution due to the presence of residual cell fragments. In one embodiment of the present invention, an in-line purification device, such as a line-driven capillary located just prior to the sample inlet of a flow cytometer as shown in FIG. 3, is used to transport large particles of interest 30 (e.g. lymphocytes) to central axis 32 of the sample stream while smaller particles 34 such as cellular debris and proteins contained within the lysate remain unaffected. This is especially true for cellular debris with less mechanical contrast than the particles of interest. The central core of the sample stream is then fed into the flow cytometer and the remaining lysate is discarded eliminating a large particulate concentration from the sample. It should be noted that this method of sample preparation can be used as a sample purification step for any type of particle/cellular analysis where the reduction of background particulate count is advantageous Particle Orientation in a Standing Acoustic Wave Field Example 1

To demonstrate the effects of the acoustic field to induce deterministic particle orientation, experiments using particles with aspect ratios greater than unity were conducted with a line driven capillary. In one example, the capillary was made of glass and had an by inner diameter of approximately 500 pm and an outer diameter of approximately 1000 pm. An acoustic source was attached to the outer surface of the capillary (parallel with the axis of the capillary) and operated at approximately 1.78 MHz and approximately 10 Vpp. A suspension of circular cylindrical carbon fibers in deionized water was transported down the tube with a syringe pump. The particles were then imaged through a microscope. The fibers had a minor axial dimension of approximately 8 pm with varying greater major axis dimensions.

Figure 4A:
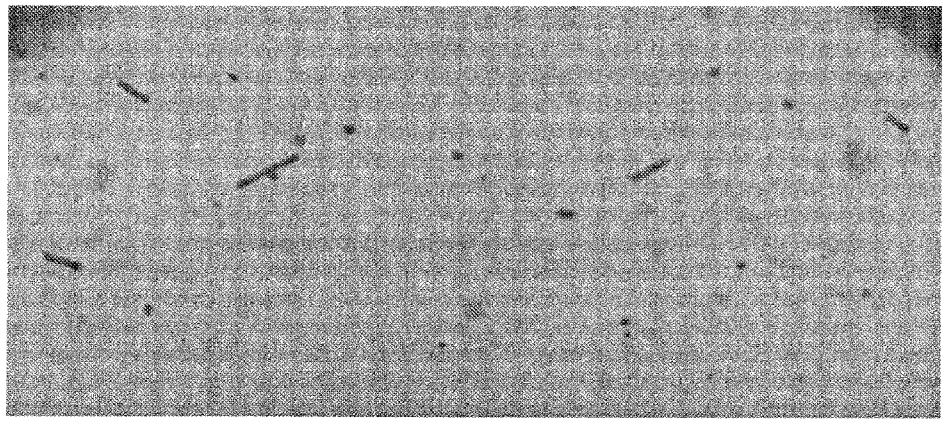
FIGS. 4A and 4B illustrate particles flowing through a capillary in a random orientation when the acoustic field is off and then particles aligned coincident with the capillary axis upon excitation of the acoustic field according to one embodiment of the present invention.
Figure 4B:
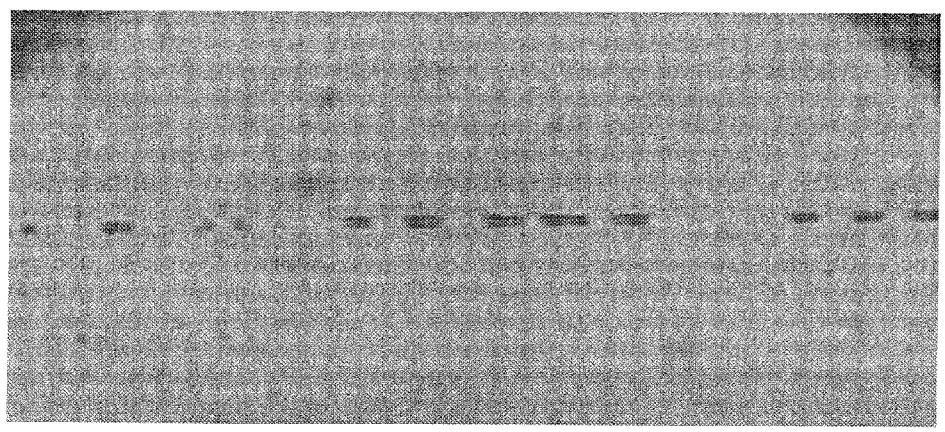

FIG. 4A illustrates the sample as it flowed through the capillary (flow is from left to right). Fibers were seen in random orientations as they were entrained in the fluid and transported through the system when no acoustic field was present. Upon acoustic excitation of the capillary, the fibers were transported and rotated to align coincident and parallel with the axis of the capillary, see FIG. 4B. The alignment shown here was due to the acoustic radiation pressure force aligning the major axis of the particles along the axis of the capillary.

Field-Based Particle Size Selection for In-Line Sample Purification and Separation/Concentration By varying the drive voltage and/or the frequency of excitation of the acoustic source in an acoustically driven capillary, a binary fractionation of particles by size can be achieved. This effect is a result of the reduced acoustic force felt by the smaller particles due to the cubic dependence of the acoustic force on particle radius. In application, the larger particles contained within the central core of the capillary are fed into a smaller, coaxial capillary discarding the concentric flow field containing small particulates. The purified sample can be taken for further sample preparation steps or fed real-time into a flow cytometer or other means of analysis. Depending upon the application, the fluid outside the central core may also be considered a valuable sample to be collected and used for analysis.

Example 2

Figure 5A:
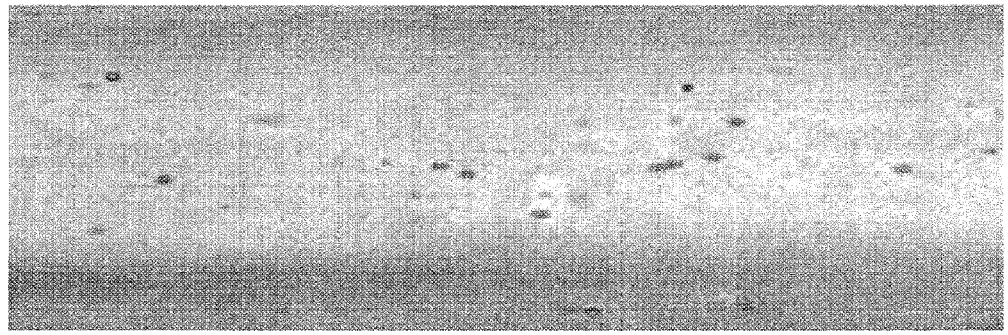
FIGS. 5A-5C illustrate selective fractionation of particles that are approximately 1 pm and approximately 10 pm in a line drive capillary according to one embodiment of the present invention.
Figure 5B:
Figure 5C:
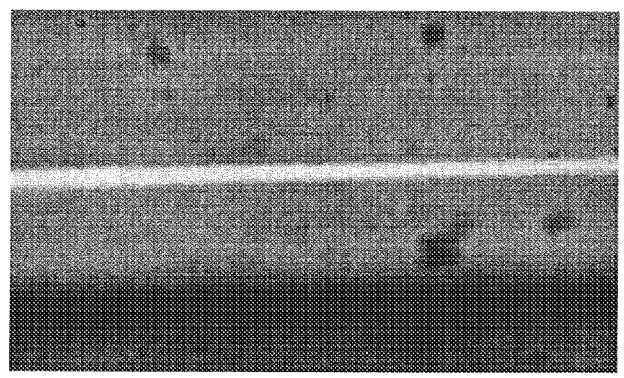

Results from preliminary experiments demonstrating the size selection capability as a function of drive level are illustrated in FIGS. 5A-5C. In this example, an acoustically driven capillary was oscillated at approximately 1.78 MHz. A suspension of latex microspheres containing approximately 1 pm diameter fluorescent spheres and approximately 10 µm diameter non-fluorescent spheres are pumped through the driven capillary. The volume fraction of particles was approximately $2.5 \times 10^{-5}$. The capillary is defined by an inner diameter of approximately 500 pm and outer diameter of approximately 1000 pm.

FIG. 5A Is a photograph taken through a fluorescence microscope where the approximately 10 pm particles are viewed as large circular inclusions and the approximately 1 µm particles are viewed as a grainy background. (The fluorescence signal from the approximately 1 pm particles is too low to be observed under the operating conditions of the experiment.) Under low acoustic drive level of approximately 7 $V_{pp}$ (FIG. 5B), the approximately 10 µm particles rapidly transported to the axis of the capillary. The approximately 1 µm particles remained randomly distributed. Doubling the drive voltage to approximately 16 $V_{pp}$ resulted in efficient transport of both sized particles to the central axis of the capillary, see FIG. 5C. The bright line along the axis of the cylinder was a result of the large, local increase in fluorescence due to the concentration of the approximately 1 µm fluorescent particles at that location.

Acoustic Focusing/Orientation Such as the Effects of Reflection Symmetry on Optical Scatter Parameters in an Acoustically Focused Flow Chamber An embodiment of the present invention addresses angular scattering associated with particles that are aligned in the optical scattering plane as a result of acoustic radiation pressure. The replacement of hydrodynamic sheath flow with acoustically driven particle alignment in a flow cell preferably leads to improved light scatter data and yields new parameters that are dependent upon particle geometry and orientation. In addition to the importance of particle orientation of asymmetric biological particles (e.g. RBC's, sperm cells, bacteria) in flow cytometry analysis, complex geometries that are formed from the coalescence of multiple microspheres or cells (e.g. 'dumb bell' shapes from agglutination of two particles) also benefit from particle orientation. Particle clusters are preferably more easily discriminated by having their orientation fixed in the scattering plane. Orienting microsphere 'doublets' to yield repeatable and unique scattering signatures due to how they transit the scattering plane will provide a means to isolate their contribution in optical scattering data for either data rejection or data acceptance by utilizing the solution of the inverse scattering problem for contacting spheres. The application of acoustically oriented particles in a flow stream is also applicable to the field of imaging where viewing selected orientations of particles is valuable in determining cellular morphology, localization of cellular constituents, or other particle/cellular characteristics.

Enhanced Detection Capabilities Under Slow-Flow, Stop-Flow, and Reverse-Flow Conditions in Acoustically Focused Flow Chambers Another embodiment of the present invention further addresses the effects of slow-flow, stop-flow, reverse-flow, and increased analysis times in flow cytometry, detection that result from replacing sheath flow with acoustic particle alignment. In the first instance, the ability to stop and reverse the flow direction of the sample stream allows for particles to be reanalyzed. The flow is stopped and/or reversed using various stop flow and reverse flow devices, including but not limited to, a pump or one or more valves. Peak spread (increased Mrs) and data points that are outliers in the analysis plane are system dependent quantities that are a function of laser stability, quality of particle alignment, electronic noise, detector noise, robustness of the assay (on/off rates, etc.), etc. By analyzing a particle of significance more than once, the data quality can be improved (especially in the case of transient artifacts) and the statistical uncertainties in rare event analysis can be minimized.

Figure 6:
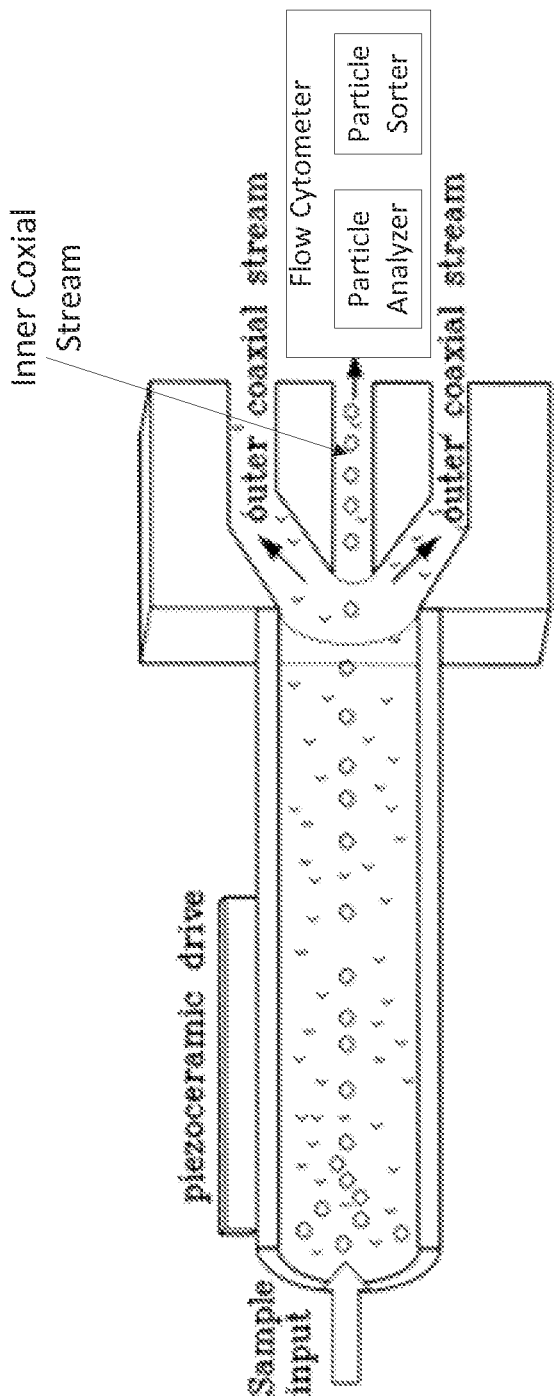
FIG. 6 is an embodiment of the present invention illustrating a sample input into a flow cytometer where the sample is concentrated reducing its volume and thus reducing the analysis time in flow cytometry applications.

Acoustic Field-Based Particle Size Selection for In-Line Sample Purification and Particle Isolation While acoustic focusing is useful for particle or cell analysis by replacing sheath flow in the detection system, yet another embodiment of the present invention extends the application of acoustic forces in acoustically driven capillaries to particle and/or cell separations for upstream, in-line sample conditioning in flow cytometry systems or general sample preparation and purification. FIG. 6 illustrates utilizing the present invention to acoustically size fractionate (and concentrate) samples by particle size and/or mechanical contrast relative to the background medium in real-time at the inlet of a flow cytometer before the analysis stage. Direct fractionation based upon particle size/mechanical properties alleviates the need for labor intensive sample preparation steps that include centrifugation and filtering. For flow cytometry applications, this is useful in reducing the background associated with cellular debris, proteins, and other molecular components in whole blood assays, and in particular, no-wash assays that include cellular lysis. A sample preparation including a cellular debris rejection step prior to sample delivery into the flow cytometer can greatly reduce artifacts associated with scatter/fluorescence from the debris.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. A method for acoustically manipulating one or more particles, comprising:
   flowing, along a flow axis, a fluid containing particles therein;
   applying acoustic radiation pressure to the fluid and acoustically manipulating the one or more particles;
   acoustically orienting the particles so as to place the particles into substantially the same rotational orientation as one another and so as to place the particles into substantially the same rotational orientation relative to the flow axis; and
   reviewing at least one of the particles.

2. The method of claim 1, wherein reviewing comprises analyzing at least one of the particles.

3. The method of claim 1, wherein reviewing comprises sorting at least one of the particles.

4. The method of claim 1, comprising flowing the fluid through a flow cytometer.

* * * * *